United States Patent [19]
Anthony

[11] Patent Number: 5,957,686
[45] Date of Patent: Sep. 28, 1999

[54] INCISOR BLOCK

[76] Inventor: Wayne L. Anthony, 111 West Newport Rd., Lititz, Pa. 17543

[21] Appl. No.: 09/064,428

[22] Filed: Apr. 22, 1998

Related U.S. Application Data

[60] Provisional application No. 60/045,088, Apr. 29, 1997.
[51] Int. Cl.⁶ .................................................. A61C 3/00
[52] U.S. Cl. .............................. 433/19; 433/215; 433/24; 433/6
[58] Field of Search ................................. 433/215, 2, 18, 433/19, 6, 24

[56] References Cited

U.S. PATENT DOCUMENTS

| | | | |
|---|---|---|---|
| 4,419,992 | 12/1983 | Chorbajian | 433/6 |
| 4,480,994 | 11/1984 | Hoffman | 433/3 |
| 4,915,630 | 4/1990 | Honig | 433/215 |
| 4,950,158 | 8/1990 | Barngrover et al. | 433/18 |

OTHER PUBLICATIONS

The Levy Lingual Shelf, Philip H. Levy DDS, Journal American Academy, Gnath. Orthopedics, Jun. 1984.
Physiologic Response to Dental Malocclusion and Misplaced Mandibular Posture: The Keys to Temporomandibular Joint and Associated Neuromuscular Disorders, Philil H. Levy, DDS, Basil Facts, vol. 4, No. 4.

*Primary Examiner*—John J. Wilson
*Assistant Examiner*—Patrick A. Hilsmier
*Attorney, Agent, or Firm*—Dan Williams

[57] ABSTRACT

An incisor block for mounting on the lingual surface of an incisor to produce separation between the upper and lower posterior teeth in deep bite patients. The incisor block has a block body and a positioning cap. The block body has a mounting surface designed to closely abut the lingual surface of the incisor, a biting surface and a thickness. Proximate to the incisor and extending toward the incisal surface when the block is mounted on the incisor is a positioning cap having a notch and a facial extension. Ferromagnetic recovery fragments may be positioned within the block body and positioning cap. The block is installed on the incisor by the method of first etching the tooth before placing an adhesive bonding agent on the etched tooth surface and the mounting surface of the incisor block. The incisor block is placed into position by placing the positioning cap against the incisal edge and pressing the mounting surface against the incisor's lingual surface. Positive placement is facilitated by engagement of the notch with the incisal edge. Once the adhesive is cured, the positioning cap of the incisor block may be fractured off with pliers and then trimmed to remove any rough material from the block body.

7 Claims, 2 Drawing Sheets

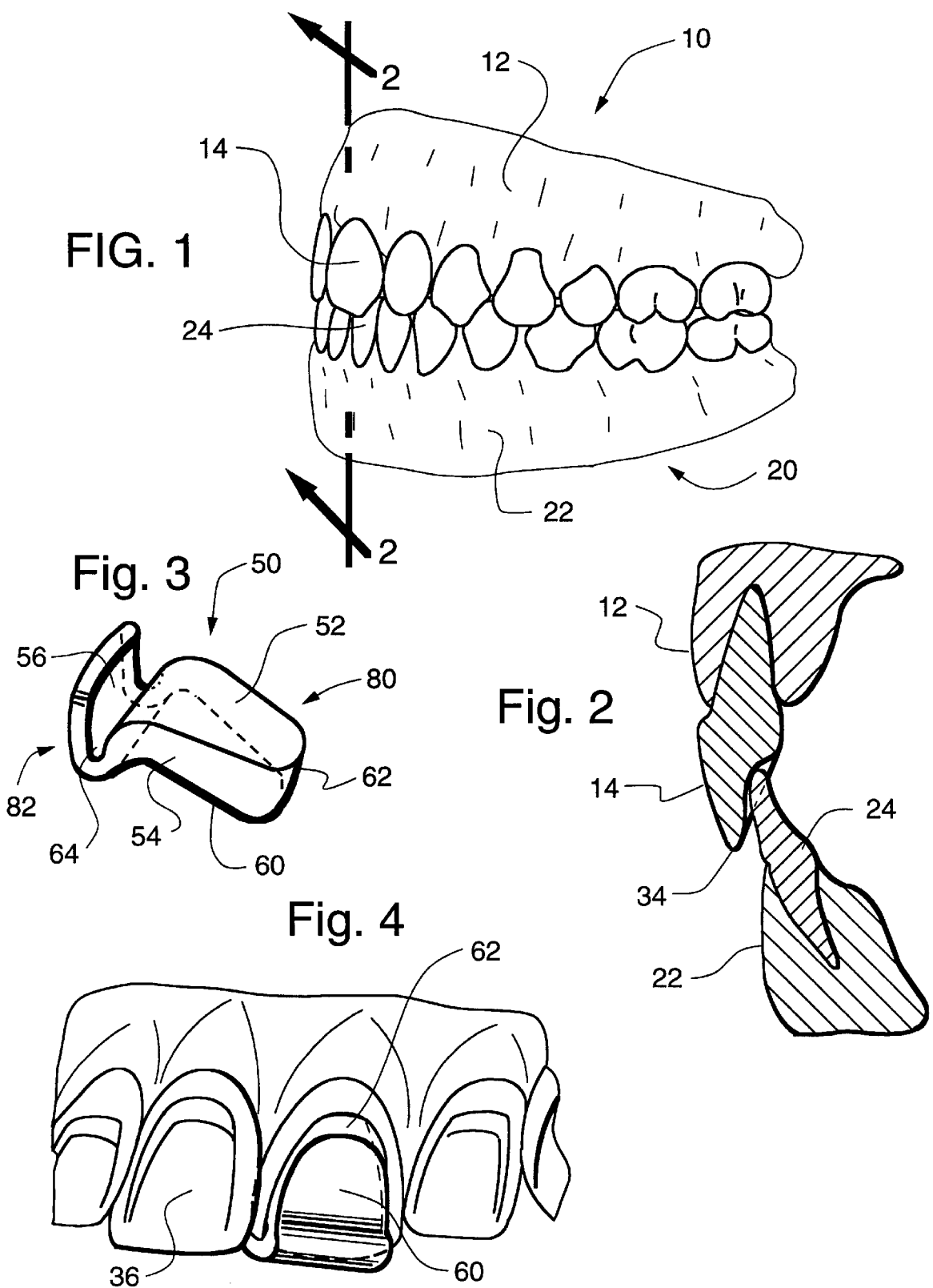

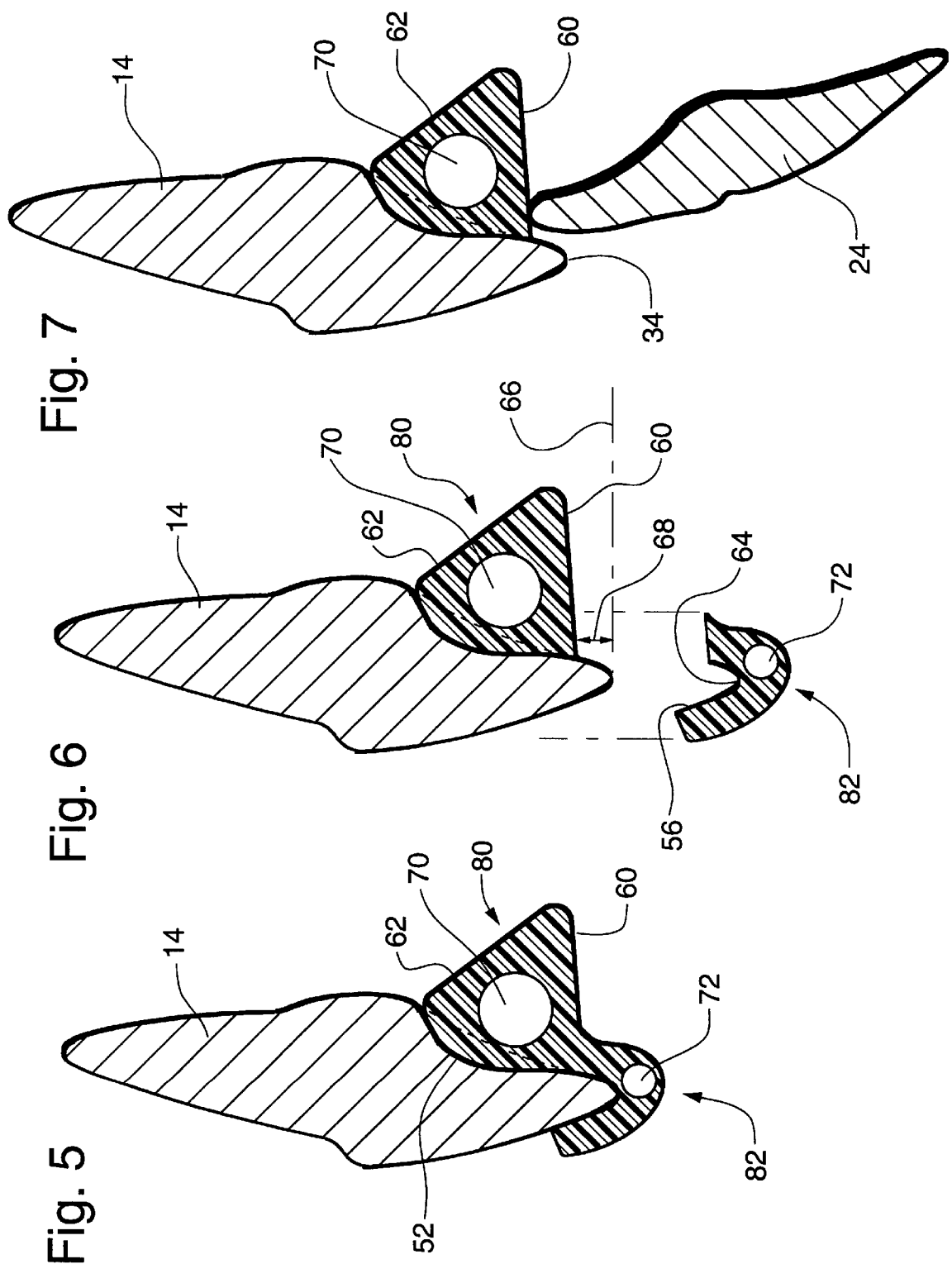

INCISOR BLOCK

This application claims the benefit of U.S. Provisional Application No. 60/045,088, filed Apr. 29, 1997.

BACKGROUND

1. Field of the Invention

The present invention relates to an incisor block. More particularly, the present invention relates to an incisor block with a removable cap that allows quick and easy placement of the incisor block on the maxillary anterior teeth.

2. Description of the Related Art

Decreasing deep anterior overbites is a problem often faced by orthodontic practitioners. Deep anterior overbites can be reduced to an ideal relation by extruding the posterior teeth toward one another. After sufficient extrusion, the posterior and anterior teeth occlude to form a "level" bite and the overbite can be reduced to 1 mm which is thought to be most desirable by many practitioners.

It is well known that individuals can exert significant pressure on the posterior grinding teeth but can exert relatively little pressure on the anterior teeth, particularly the incisors. The effect of this trait is to make it more difficult to extrude the posterior teeth to accomplish a level bite.

Practitioners face another problem with patients having excessive overbite ("deep bite patients") in that orthodontic braces on the facial surface of the lower teeth are often knocked off by the biting forces of the patient. This is because occlusion is done on the braces rather than with the maxillary teeth.

Hoffman, U.S. Pat. No. 4,480,994 describes an orthodontic occlusion prevention system in which a plate of material is positioned over selected maxillary anterior teeth. The plate prevents occlusion between the upper and lower posterior teeth. The plate is anchored by connection to sheaths that are connected to molar jackets. The difficulty with this system is that it involves a complicated support structure, is relatively large and cumbersome and, in this age of appearances, is readily noticeable in the mouth of the wearer.

Chorbajian in U.S. Pat. No. 4,419,992 describes a two layer occlusal splint in which a soft resilient layer is molded to conform to the posterior surface of the maxillary anterior tooth. The second layer is a hard acrylic resin mounted on the first layer. The hard resin is designed so that several lower teeth strike the splint at the same time, thereby equalizing and minimizing the pressure on the lower teeth. The splint is resiliently retained on the upper teeth by a snap fit. This splint is said to alleviate tempro-mandibular joint dysfunction. Because the splint extends around to the exterior surface of the anterior teeth, the splint is readily noticeable in the wearers mouth.

A recently developed innovation involves cementing pieces of acrylic on the lingual surfaces of at least two maxillary anterior teeth. These pieces of acrylic are not noticeable in the wearers mouth. Placement of these acrylic pieces can be a very challenging clinical procedure due to several factors.

The first factor is that the lingual surfaces of most maxillary incisors have very little anatomy to facilitate bonding the appliance without the appliance moving during the bonding procedure or during flash cleanup. The second factor is that the retro-inclination of the maxillary anterior teeth confronted in a typical Class II division 2 malocclusion where deep bites are almost always present presents difficulty for the practitioner to gain access and visibility.

An incisor block should be capable of being precisely formed and then precisely positioned within the mouth. Ideally, the form can be made on a mold of the teeth and the block can be formed prior to actually working in the patients mouth. The block should be formed to limit overbite to approximately 1 mm; an overbite which is considered ideal to most practitioners. Finally, the device should be capable of being rapidly and positively positioned within the mouth. In this way, adhesive, cement or other types of bonding agents can be applied to the incisor block before insertion. After the block is precisely inserted in the correct position, the block must be capable of being easily held in position while the adhesive cures.

SUMMARY OF THE INVENTION

One object of the present invention is to provide an anterior overbite reduction device that can assist in eruption of posterior teeth. One result of using the device is gaining separation between the upper and lower posterior teeth.

Another object of the present invention is to provide a device that can be quickly and easily placed and cemented to the inside surface of the anterior maxillary teeth. Application of cement should take place before the device is placed in the mouth. Placement of the device should be by positively locking or snapping the device into a discrete location and failure to place the device in the correct location should be readily apparent either by feel or by visual inspection.

Still another object of this invention is that patients should be unable to tamper with the device. Devices that involve wiring and support from other areas in the mouth can sometimes be defeated by actions of the wearer.

Yet another object of the present invention is that the device provide minimal interference with oral hygiene. Corners and places where food can collect should be avoided when appliances are constructed.

Another object of the present invention is to provide overbite correction to about 1 mm. Many practitioners consider an overbite of about 1 mm to be the most desirable although other practitioners consider satisfactory overbites to range between 0 and 5 mm.

Still another object of the invention is to provide means by which the device can be found and recovered in the event the device or part of the device thereof is swallowed or inadvertently enters other passages in the mouth from which extraction is difficult.

These and other objects can be provided by a device that can be easily placed and semi-permanently bonded to the lingual surface of the maxillary anterior teeth for the purpose of gaining separation between the posterior teeth in anterior deep bite patients. The device can be fabricated to provide for the desirable 1 mm overbite and can be customized to fit the particular shape of the wearers maxillary incisor's lingual surface. Positive location can be provided by a positioning cap that positions the device with respect to the incisal edge. Excess positioning cap material can easily be removed with a burr. The result is an easily placed and fastened incisor block that is not apparent to an external observer.

The incisor block may be custom fabricated to the inner contour of the incisor to which it is fitted. To facilitate fabrication, a mold is made of the wearers incisor region. The block is fabricated to fit precisely on the mold. Alternatively, stock incisor blocks can be prefabricated in several sizes, each size to fit a range of tooth sizes, and then custom fitted by the practitioner at the time the block is installed on the tooth.

The incisor block is a shaped device comprising a block body and a positioning cap. The block body has a mounting surface, a biting surface and a heel. The mounting surface is fabricated to fit on the lingual surface of the incisor to which it is to be cemented. The lower incisor strikes the biting surface and is prevented from further closure. At this point, the posterior teeth are separated by a gap thus passively allowing the posterior teeth to extrude. Naturally, other dental appliances may be fitted to expedite extrusion of the posterior teeth.

The incisor block has a positioning cap formed by continuing the mounting surface around the incisal edge of the incisor a sufficient distance to form a mounting notch in the block. The incisal edge of the maxillary incisor rests in the notch. The positioning cap can be extended up the facial tooth surface as far as necessary to facilitate the tooth seating securely in the notch.

The block body has a thickness within which a ferromagnetic fragment may be inserted during fabrication of the incisor block. The block body remaining in the mouth after semi-permanent bonding to the tooth has a volume, the periphery of which is defined by the mounting surface, biting surface and heel. Within the block body, a small volume of ferromagnetic material may be installed. If the incisor block falls off the tooth and finds its way into passages from which recovery is difficult without surgery, a magnetic probe may be used to attract the ferromagnetic material in the incisor block and thus aid extraction.

The positioning cap also has a volume within which ferromagnetic material may be installed to facilitate removal in the event the mounting notch falls into the patients mouth and is swallowed or otherwise moves to an area from which extraction is difficult.

The incisor block is cemented on the tooth in a manner well known in the art. The maxillary incisor is etched on the lingual surface and a dab of bonding adhesive is placed on the block and the etched tooth surface. The block is then inserted on the tooth.

When using stock incisor blocks that are not custom fabricated to the wearers tooth structure, the installation procedure is modified to include preliminary application of acrylic or filler adhesive to the interface between the incisor block and tooth surface.

It is important that, during the final adhesive bonding stage when the block is being semi-permanently attached to the tooth, that the block be cemented only on the lingual tooth surface at a distance more than the targeted overbite from the incisal surface. When done in this fashion, the positioning cap is not cemented or fastened to the tooth.

After the block has been semi-permanently attached and the bonding adhesive is cured, the positioning cap can be removed with a burr or by cutting a kerf at the junction of the biting surface and positioning cap and then fracturing the positioning cap off with Howe or Weingart pliers.

BRIEF DESCRIPTION OF THE DRAWINGS

These and other features, aspects, and advantages of the present invention will become better understood with regard to the following description and accompanying drawings where:

FIG. 1 is left side view of a normal jaw showing the position of the teeth;

FIG. 2 is a partial cross section view through the gum and anterior tooth structure of FIG. 1 showing a deep overbite condition;

FIG. 3 is a perspective view showing my new incisor block with positioning cap;

FIG. 4 is a view from inside the mouth looking outwardly showing the position of my incisor block when installed on a maxillary incisor tooth;

FIG. 5 is cross section view of the maxillary incisor of FIG. 2 after my new incisor block has been installed;

FIG. 6 is a cross section view of the maxillary incisor of FIG. 2 after the incisor block has been installed and the positioning cap removed; and FIG. 7 is a cross section of the incisors of FIG. 2 after installation of the incisor block showing the lower incisor contacting the incisor block.

DESCRIPTION

Although the disclosure herein is detailed and exact to enable those skilled in the art to practice the invention, the physical embodiments herein disclosed merely exemplify the invention which may be embodied in other specific structures.

The incisor block is essentially a hard formed device, installed on the lingual surface of maxillary incisors, that is designed to reduce deep anterior overbites. The block may be fabricated from any moldable hard wear resistant material. In the preferred embodiment, incisor blocks are fabricated from acrylic plastic.

As better seen in FIG. 1, upper jaw 10 and lower jaw 20 are surrounded by maxillary facial gingiva 12 and lower facial gingiva 22. On the upper jaw, maxillary left central incisor 14 is used as the example tooth on which the block is mounted. On a normal jaw, there are eight incisors and the incisor block can be mounted effectively on any maxillary or mandibular central or lateral incisor, however, for simplicity, the block is described as being mounted on maxillary left central incisor 14. Maxillary left central incisor 14 and mandibular left central incisor 24 correspond to each other in that mandibular incisor 24 rests against the lingual surface of maxillary incisor 14 when the jaw is closed.

FIG. 2 is a cross section view through maxillary incisor 14 and mandibular incisor 24 in a patient with deep anterior overbite. When the jaw is closed, mandibular incisor 24 rests against maxillary incisor lingual surface 36. As seen in FIG. 2, incisal edge 34 of maxillary incisor 14 is well below the incisal edge of mandibular incisor 24.

Incisor block 50 and it's position during and after installation are better seen in FIG. 3–FIG. 7. Incisor block 50 is comprised of two integrally fabricated regions, block body 80 and positioning cap 82. The first region, block body 80, has a mounting surface 52 and biting surface 60 separated by block thickness 54. The block thickness will vary according to the patients tooth size and shape as well as overbite and overjet. The incisor block width is approximately two thirds of the mesio-distal width of the lingual surface of the incisor to which it will be inserted.

Mounted within block body 80 is block recovery fragment 70. Similarly, cap recovery fragment 72 is embedded within positioning cap 82. The recovery fragments are pieces of ferromagnetic material attractive to a magnetic probe. In the event either block body 80 or positioning cap 82 becomes dislodged or falls into the patients mouth and is subsequently swallowed or moves to a position from which it cannot be readily recovered, a magnetic probe can be used to attract fragments 70, 72 and facilitate their removal. The ferromagnetic material is also radio opaque in the event X-Rays are needed to locate the block body or positioning cap. A 1/16" to 1/8" diameter ball bearing has been found useful for block recovery fragment 70. A smaller size is required for the cap recovery fragment.

Biting surface 60 is positioned at desired overbite distance 68 gingival to occlusal plane 66. Distance 68 is the patients optimum overbite which most practitioners approximate at one millimeter. The overall length of biting surface 60 between the lingual surface of maxillary incisor 14 and heel 62 need only be long enough so that lower incisor 24 contacts biting surface 60 instead of sliding behind heel 62. The required length of the biting surface varies with the amount of overjet present in that patient.

The second region of incisor block 50, positioning cap 82, is comprised of notch 64 and facial extension 56. Notch 64 begins at the intersection of biting surface 60, extending to incisal edge 34 and continues as facial extension 56 on the facial surface of incisor 14. Alternatively, facial extension 56 can be minimized or even eliminated as long as notch 64 provides a positive stop or ledge against which incisal edge 34 can be located. Positioning cap 82 is thick enough to be sufficiently rigid to withstand moderate finger pressure without permanent deformation.

In the preferred embodiment, mounting surface 52, notch 64 and extension 56 are formed on a mold of the patients tooth. The result is that mounting surface 52, notch 64 and extension 56 fit the exact contour of the patients tooth and incisor block 50 may be placed on the tooth in the precise location at which it is to be bonded. This greatly expedites precise installation of incisor block 50 on the tooth.

Incisor blocks may also be prefabricated in a series of sizes that span a range of tooth sizes. These universal blocks may be custom fitted to the patients tooth structure and installed in one office appointment. The primary disadvantage with universal blocks is that placement of the block is not as precise as if the blocks are custom fabricated from a mold of the patients teeth.

When customizing a prefabricated universal block, mounting surface 52 and notch 64 are first coated with a liquid monomer. Either a cold cure or light cured acrylic adhesive is liberally applied over surface 52 and notch 64. Notch 64 is positioned against incisal edge 34 and finger pressure applied on biting surface 60 and positioning cap 82 to press mounting surface 52 against the lingual tooth structure. Excess acrylic adhesive oozing from the interface between mounting surface 52 and the lingual tooth surface forms a flash. After curing a few minutes, the block is removed and the flash removed. After further curing, the now custom fitted block is inserted on the tooth as if the block had been originally custom fitted from a mold and the block is ready for semi-permanent installation.

It is also possible to install universal blocks without customizing the block for a particular tooth. An excessive amount of bonding material must be used when inserting in this fashion, thus direct installation of universal blocks is not as precise and is a less desirable installation technique. Direct installation also results in weaker bond strength since excessive amounts of bonding material must be used.

Incisor block 50 is now installed on the tooth by adhesive and bonding methods well known in the art. The first step is to etch the lingual tooth surface to which the block is to be attached. Concurrently, a liquid monomer is painted on mounting surface 52. A two part liquid—liquid cold cure bonding adhesive is applied to mounting surface 52 and the etched tooth area. No adhesive is applied to notch 64 or the corresponding region of the tooth. Finally a dab of two part paste-paste cold cure bonding adhesive is applied to mounting surface 52. Notch 64 may now be positioned against incisal edge 34 of the maxillary incisor to which the block is to be mounted. Once notch 64 is positioned against incisal edge 34, finger pressure on biting surface 60 and positioning cap 82 is used to press mounting surface 52 against the lingual tooth surface.

FIG. 5 illustrates a cross section of the tooth and block 50 after the block has been semi-permanently installed. Positioning cap 82 of block 50 is now removed. Since no adhesive was applied to cap 82, cap removal can be easily accomplished with a dental burr. A kerf is cut into positioning cap 82 parallel to and adjacent to biting surface 60. The kerf may extend almost to the tooth leaving a small amount of block material between the tooth and the kerf. With a minimal amount of material holding notch portion 82 to block portion 80, notch portion 82 may be easily fractured off with either Howe or Weingart pliers. Any remaining material is easily visible and accessible and may be removed with a small round burr. The remaining block portion 80 is seen in FIGS. 6 and 7. If biting surface 60 extends too far posterior in the mouth, surface 62 can be trimmed back with a burr.

It should be noted and remembered that incisor blocks can be inserted on lower incisors for class III deep bite malocclusions in the same fashion as described herein.

It should be also be remembered that there are numerous commercially available adhesive bonding materials designed for orthodontic practitioners. Although the systems described herein are preferred, light cured hard setting systems and two part cold curing systems are largely interchangeable and the exact selection of the adhesive bonding system is at the discretion of the practitioner. The primary considerations are that the tooth area not be etched until the block is ready for final semi-permanent installation and that a filler type of adhesive be used when making the semi-permanent installation.

The blocks can be removed when posterior teeth once again come together in occlusion. If the blocks cannot be easily removed in the same manner as removal of orthodontic brackets, they can be removed with a round burr.

Many modifications and variations of the above invention is possible. It is therefore understood that the invention may be practiced otherwise than as specifically before described and still fall within the scope of the claims.

What is claimed is:

1. An incisor block to aid posterior tooth eruption to a desired occlusal plane by mounting on the lingual surface of an incisor, said incisor block comprising:

a. a block body defined by a mounting surface, a thickness, and a biting surface, said biting surface defining a plane substantially parallel to said occlusal plane when said mounting surface is proximately attached to said lingual surface;

b. a positioning cap attached to said block body, said positioning cap being attached to said block body at a notch; and c. a block recovery fragment embedded wholly within the interior of said block body.

2. The incisor block of claim 1 further comprising a cap recovery fragment embedded within said positioning cap.

3. The method of installing an incisor block on an incisor having an incisal edge and a lingual surface, said incisor block comprising a block body and a positioning cap, said block body having a mounting surface, thickness and a biting surface, said positioning cap having a notch, said method comprising:

a. etching said lingual surface of said incisor;

b. applying adhesive to said mounting surface while leaving said positioning cap free of adhesive;

c. positioning said notch against said incisal edge;

d. pressing said incisor block against said lingual surface;

e. allowing said adhesive to cure; and f. removing said positioning cap from said block body.

4. The method of installing an incisor block of claim 3, further comprising the step of embedding a block recovery fragment wholly within said block body before etching said lingual surface.

5. The method of installing an incisor block of claim 3, further comprising the step of mounting a cap recovery fragment within said positioning cap before etching said lingual surface.

6. An incisor block comprising:

a. a block body defined by a mounting surface, a thickness, and a biting surface;

b. a positioning cap attached to said block body, said positioning cap being attached to said block body at a notch; and c. a block recovery fragment embedded within said positioning cap.

7. The incisor block of claim 6 further comprising a block recovery fragment embedded within said block body.

\* \* \* \* \*